United States Patent [19]

Bromander

[11] Patent Number: 5,100,385
[45] Date of Patent: Mar. 31, 1992

[54] FAST PURGE BALLOON DILATATION CATHETER

[75] Inventor: Roy C. Bromander, Reading, Mass.

[73] Assignee: C. R. Bard, Inc., Murray Hill, N.J.

[21] Appl. No.: 590,339

[22] Filed: Sep. 28, 1990

Related U.S. Application Data

[63] Continuation of Ser. No. 303,647, Jan. 27, 1989, abandoned.

[51] Int. Cl.⁵ .............................................. A61M 29/00
[52] U.S. Cl. ........................................ 604/99; 606/194
[58] Field of Search ................................ 604/96–103, 604/52, 53, 164, 167, 246; 606/192–196; 128/207.15–207.17

[56] References Cited

U.S. PATENT DOCUMENTS

| | | | |
|---|---|---|---|
| 3,402,717 | 9/1968 | Doherty | 604/99 X |
| 3,402,718 | 9/1968 | Doherty . | |
| 3,417,750 | 12/1968 | Carson | 128/278 |
| 3,527,226 | 9/1970 | Hakim | 128/350 |
| 3,592,184 | 7/1971 | Watkins et al. | 128/1 R |
| 3,707,151 | 12/1972 | Jackson | 128/351 |
| 3,726,283 | 4/1973 | Dye et al. | 604/99 |
| 3,742,960 | 7/1973 | Dye et al. | 128/349 BV |
| 3,888,249 | 6/1975 | Spencer | 128/214 R |
| 4,014,317 | 3/1977 | Bruno | 128/1 D |
| 4,323,071 | 4/1982 | Simpson et al. | 128/343 |
| 4,351,341 | 9/1982 | Goldberg et al. | 128/348 |
| 4,411,055 | 10/1983 | Simpson et al. . | |
| 4,413,989 | 11/1983 | Schjeldahl | 604/96 |
| 4,549,879 | 10/1985 | Groshong et al. | 604/247 |
| 4,582,181 | 4/1986 | Samson | 606/194 |
| 4,597,755 | 7/1986 | Samson et al. | 604/96 |
| 4,606,347 | 8/1986 | Fogarty et al. | 606/194 |
| 4,638,805 | 1/1987 | Powell | 128/344 |
| 4,665,925 | 5/1987 | Millar | 128/663 |
| 4,684,363 | 8/1987 | Ari et al. | 604/98 |
| 4,715,378 | 12/1987 | Pope, Jr. et al. | 128/344 |
| 4,762,129 | 8/1988 | Bonzel | 128/344 |
| 4,793,351 | 12/1988 | Landman et al. | 128/344 |
| 4,811,737 | 3/1989 | Rydell | 128/344 |
| 4,813,934 | 3/1989 | Engelson et al. | 604/99 |
| 4,848,344 | 7/1989 | Sos et al. | 128/344 |
| 4,932,959 | 6/1990 | Horzewski et al. | 606/194 |
| 4,943,278 | 7/1990 | Euteneuer et al. | 604/96 |
| 5,035,705 | 7/1991 | Burns | 606/194 |

FOREIGN PATENT DOCUMENTS 3625871 2/1988 Fed. Rep. of Germany .

Primary Examiner—John D. Yasko
Assistant Examiner—Adam Cermak
Attorney, Agent, or Firm—Wolf, Greenfield & Sacks

[57] ABSTRACT

A balloon dilatation catheter having a guidewire lumen that extends to the distal tip of the catheter, a balloon mounted on the distal end of the catheter and an inflation lumen extending through the shaft and communicating with the interior of the balloon is provided with an improved arrangement for filling the inflation lumen and balloon with liquid while purging air from the system. The device includes a one-way valve means carried by the catheter shaft within the balloon which permits fluid flow from the guidewire lumen into the balloon under a predetermined pressure greater than about one atmosphere. The system is used by first plugging the distal end of the guidewire lumen and then pressurizing the guidewire lumen with inflation liquid sufficiently to open the one-way valve means to permit inflation liquid to fill the balloon. As the balloon fills, air is forced out of the balloon through the inflation lumen and is vented through the open proximal end of the inflation lumen. The one-way valve means is constructed to preclude reverse flow under pressures greater than 20 atm and to preclude opening in response to aspiration through the inflation lumen at a level not greater than 1 atmosphere pressure.

8 Claims, 2 Drawing Sheets

FAST PURGE BALLOON DILATATION CATHETER

This application is a continuation of application Ser. No. 303,647, filed Jan. 27, 1989, now abandoned.

FIELD OF THE INVENTION

This invention relates to balloon dilatation catheters.

BACKGROUND OF THE INVENTION

Balloon dilatation catheters are used for a variety of procedures in which a body lumen or vessel is dilated. For example, such catheters are used in angioplasty procedures in which a stenosed region of an artery, such as a coronary artery, is widened by inserting a deflated balloon into the stenosis and then inflating the balloon under pressure to enlarge forcibly the lumen through the artery. Such catheters typically have an elongate flexible shaft and a balloon mounted at the distal end of the shaft. The shaft has an inflation lumen that communicates from the proximal end of the catheter to the interior of the balloon at the distal end of the shaft. The catheter also has a main lumen that extends fully the length of the catheter shaft, terminating in a distal outlet at the distal tip of the shaft, beyond the balloon. The main lumen may be used to receive a guidewire as well as to provide fluid communication with the interior of the patient's artery to inject radiopaque dye into the artery to visualize it fluoroscopically or to monitor the pressure in the artery, distally of the stenosis. Typically, the balloon is inflated with a liquid which is radiopaque so that the configuration and action of the balloon may be monitored fluoroscopically during the angioplasty procedure. Use of an incompressible liquid as an inflation medium assures effective development and transmission of dilating forces to the balloon and to the stenosed region of the artery that is to be dilated.

Part of the preparation of the catheter for use involves purging air from the balloon and the inflation lumen to minimize the compressibility of the balloon fluid system. With some catheters, for example, as the type disclosed in U.S. Pat. No. 4,545,390 to Leary, a catheter first is evacuated by a syringe connected to the inflation lumen at the proximal end of the catheter. After air has been evacuated from the balloon, the inflation lumen and balloon are filled, by the syringe, with inflation liquid. Typically, one or more bubbles of air will remain entrapped in the balloon and, in an effort to purge as much air from the system as possible, it is the common practice to fill the balloon while holding the catheter with its distal end hanging down to permit the air to rise through the inflation lumen to the proximal end of the catheter where it may escape to atmosphere from the vented proximal end of the inflation lumen. Most, but not all of the air can be removed by this procedure. Usually, a small bubble of air will remain in the system.

A number of arrangements have been used to effect a more complete purge of air from the catheter. U.S. Pat. No. 4,323,071 discloses a dilatation catheter system in which a slender venting tube is passed through the inflation lumen and into the balloon. As inflation liquid is purged through the inflation lumen and into the balloon, air within the system is permitted to escape through the vent tube. After the system has been completely filled with inflation liquid and the air has been vented, the vent tube may be removed or sealed within the inflation lumen. This system for purging air from the catheter is somewhat time consuming and may be awkward in that it requires a number of manipulations of the vent tube. Additionally, there is some risk that the vent tube may damage the balloon. A further difficulty is that if a minute drop of liquid contacts the distal tip of the vent tube before purging is completed, the tube will become blocked by capillary action and may have to be replaced.

U.S. Pat. No. 4,684,363 to Ari discloses a balloon dilatation catheter having a pair of parallel inflation lumens both of which extend from the proximal end of the catheter through the catheter shaft into communication with the interior of the balloon. The catheter is filled with inflation liquid by directing the liquid through one of the inflation lumens into the balloon while permitting the other lumen to vent to the atmosphere to permit air to escape. After both inflation lumens and the balloon are filled with inflation liquid, both of the lumens are connected to the inflation/deflation device and are operated in parallel to inflate or deflate the balloon. This approach requires the use of an additional lumen which necessarily requires either that the catheter be increased in outer diameter or that the other lumens in the catheter be smaller in size, thereby diminishing their capacity. Additionally, such a three lumen catheter is more difficult to extrude particularly in the smaller sizes of such catheters.

Another approach for venting the balloon is disclosed in U.S. Pat. No. 4,692,200 in which a very small air vent passage is formed between the catheter shaft and the distal end of the balloon where the balloon is mounted to the shaft. The vent passage is small enough to permit slow leakage of air out of the balloon as inflation liquid is pumped into the balloon system but is too small to permit an undue amount of liquid to leak through the vent in the operating range of most pressures. Among the disadvantages of this purging arrangement is that it presents some risk to the patient in that before the catheter is inserted into the patient, it is deflated by aspirating through the inflation lumen. Typically, there is some delay from the time that the catheter is aspirated until the time it is actually inserted into the patient. During that time, air may be drawn into the balloon through the vent. When the balloon is thereafter inserted into the patient and inflated, the inflation pressure may drive the air out through the vent and into the patient's coronary artery, thus presenting a risk of an air embolism. Additionally, the very small vent results in a relatively slow purging procedure.

It is among the general objects of the invention to provide a catheter having an improved purge system that avoids the foregoing difficulties.

SUMMARY OF THE INVENTION

In accordance with the invention, the balloon dilatation catheter includes an elongate flexible shaft having a balloon mounted at the distal end of the shaft. The shaft includes a main guidewire lumen that extends through the shaft from the proximal end of the catheter to an outlet at the distal tip. The shaft also includes an inflation/deflation lumen that extends from the proximal end of the shaft and communicates with the interior of the balloon. In order to facilitate purging of air from the system, the portion of the shaft within the balloon is formed with a passageway through the shaft wall, such as a slit, to communicate the main lumen with the interior of the balloon. The passageway is part of a one-way valve means which permits liquid flow from the main lumen into the balloon under a predetermined pressure and precludes reverse flow at all operating pressure levels, from about one atmosphere negative pressure to as much as twenty atmospheres or more positive pressure. When setting up the catheter, in order to purge the system of air, the distal outlet end of the main lumen is blocked with a plug and then inflation liquid is forced through the main lumen under a pressure sufficient to cause the one-way valve to open and permit inflation liquid to flow into the balloon. The inflation lumen is vented to the atmosphere while liquid flows into the balloon so that air flows in a proximal direction through the inflation lumen and is exhausted to the atmosphere. When the balloon and inflation lumen are filled with fluid and all of the air has been purged, the distal plug is removed and the catheter is ready for use.

It is among the general objects of the invention to provide a balloon dilatation catheter in which the balloon and inflation lumen may be filled with inflation liquid while air is purged from the system.

Another object of the invention is to provide a balloon dilatation catheter having a rapid purge system which does not require additional lumens.

Another object of the invention is to provide a balloon dilatation catheter having an inflation lumen and a guidewire lumen and a one-way valve communicating the guidewire lumen with the interior of the balloon.

A further object of the invention is to provide a balloon dilatation catheter that can be purged rapidly of air and which also provides a low balloon profile.

BRIEF DESCRIPTION OF THE DRAWINGS

The foregoing and other objects and advantages of the invention will be appreciated more fully from the following further description thereof with reference to the accompanying drawings in which.

It should be noted that the drawings are not to scale and are exaggerated in a number of respects for ease of explanation and illustration.

DESCRIPTION OF THE ILLUSTRATIVE EMBODIMENTS

Figure 1:
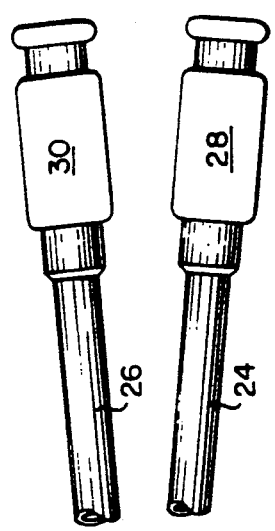
FIG. 1 is an illustration of the proximal and distal ends of one type of a balloon catheter embodying the invention when the balloon illustrated is in a deflated condition.
Figure 1:
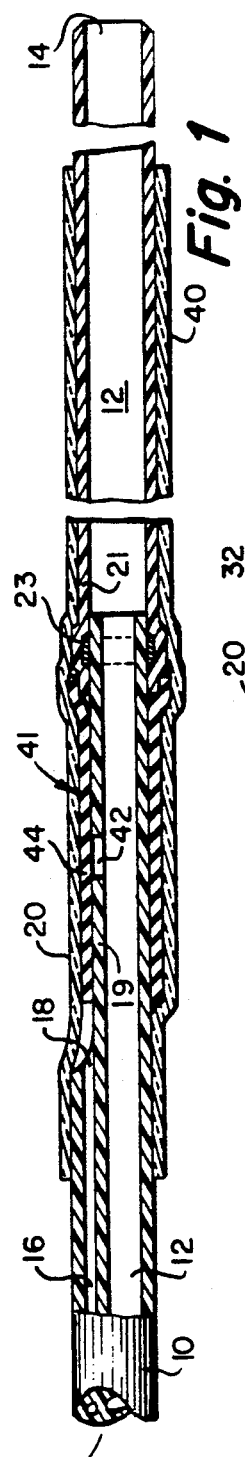
Figure 1:
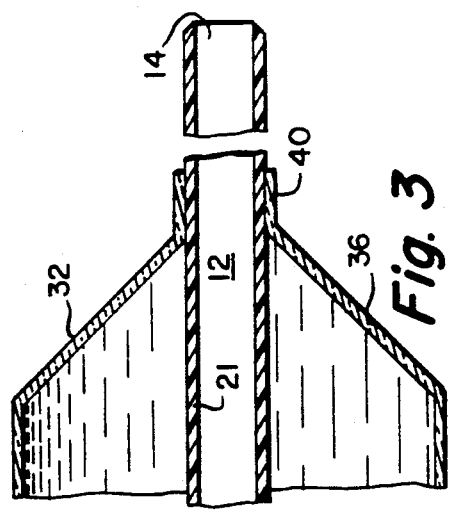
Figure 3:
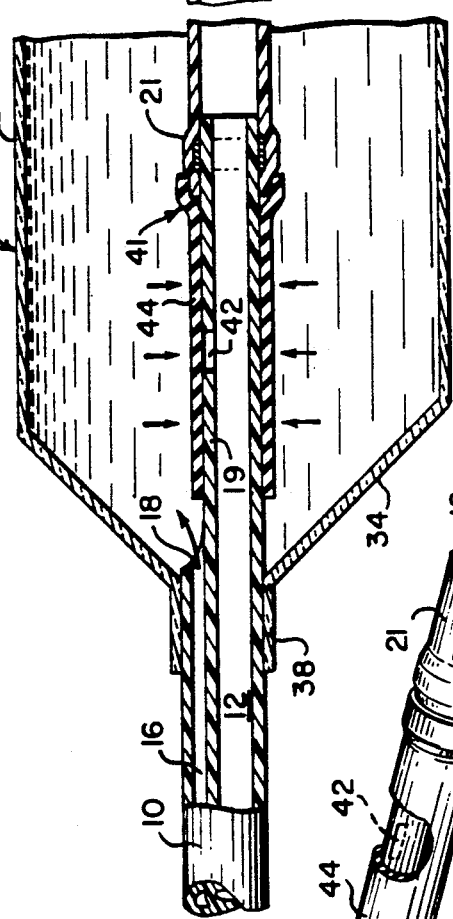
FIG. 3 is an illustration of the balloon catheter of FIG. 1 in its configuration when the balloon is inflated.
Figure 4:
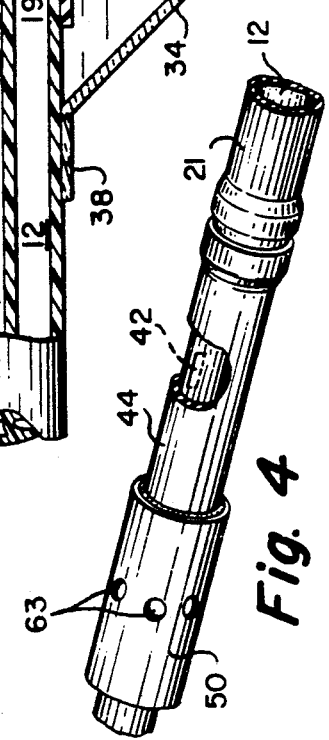
FIG. 4 is an enlarged, broken away illustration of the valving arrangement embodying the device.
Figure 2:
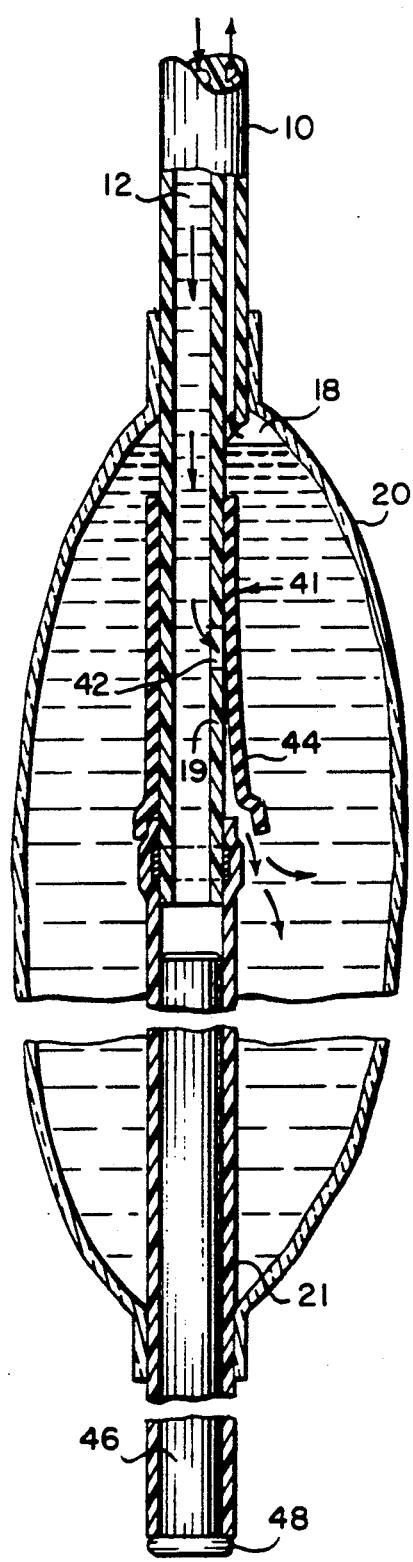
FIG. 2 is an illustration of the distal end of the balloon catheter of FIG. 1 as it is being inflated to purge air out of the system.

As shown in FIGS. 1–3, one type of construction of the balloon dilatation catheter includes an elongate flexible shaft 10 that may be formed, as by extrusion, from an appropriate plastic material such as polyvinyl chloride, polyethylene or the like. By way of example, a balloon dilatation catheter suitable for percutaneous transluminal coronary angioplasty may be of the order of 150 cm long and of the order of 0.045" (1.14 mm) outer diameter. The catheter shaft 10 has two lumens, including a main lumen 12 that extends the full length of the shaft and is open at the distal tip of the shaft at an outlet orifice 14 and an inflation/deflation lumen 16 that extends through the shaft from the proximal end to an opening 18 that communicates with the interior of the balloon 20. The distal opening 18 of the inflation lumen 16 preferably is located at the proximal end of the interior of the balloon and may be formed by skiving off the inflation lumen portion of the two lumen extrusion, leaving a single lumen tubular segment 19 distally of the opening 18. The tubular segment 19 of the shaft 10 terminates within the balloon 20 and the main lumen 12 is continued through the balloon and to the distal outlet 14 of the catheter by a single lumen tip tube 21 which may be formed from the same plastic material as the catheter shaft 10. The tubular segment 19 may have an outer diameter of 0.028" (0.71 mm) and an inner diameter, for the guidewire lumen, of 0.022" (0.56 mm). The tip tube 21 can be adhesively attached or fused to the distal end of the tubular segment 19. A highly radiopaque marker band 23 preferably is captured between the overlap of the tip tube 21 and the tubular segment 19. The tip tube 21 may have an outer diameter of the order of 0.027" (0.51 mm) and a wall thickness of about 0.0035" (0.13 mm).

The proximal end of the two lumen extrusion includes a molded transition member 22 to which the distal ends of a pair of extension tubes 24, 26 are embedded. The extension tubes 24, 26 communicate, respectively, with the main lumen 12 and inflation lumen 16. Luer fittings 28, 30 are mounted on the proximal ends of the tubes 24, 26 for connection with appropriate fluid delivery communication devices such as inflation syringe, pressure measuring device and the like.

The dilatation balloon 20 may be formed from a polymeric material adapted to be formed into a thin wall, highly flexible and relatively inelastic balloon. The balloon may be formed as described in U.S. Pat. No. 4,490,421 to Levy. The balloon includes a central cylindrical section 32 and a pair of end cones 34, 36 and mounting collars 38, 40 by which the balloon 20 is mounted to the shaft 10.

In accordance with the invention, a flow passage 42 is formed through the wall of the tubular segment 19 of the catheter shaft within the balloon 20 to communicate the main lumen 12 with the interior of the balloon 20. The flow passage preferably is in the form of a slit 42, although it may also take the form of a small hole. An elastomeric sleeve 44 is mounted on the tubular segment 19 of the shaft within the balloon to cover the slit 42 and cooperate with the slit 42 to form a one way valving arrangement, designated generally by reference character 41, which permits liquid to flow from the main lumen 12 into the balloon 20 but prevents reverse fluid flow. The slit 42 is formed through the wall of the tubular segment 19 and may be of the order of 1 mm long. Alternately, a small hole of the order of 0.010" (0.25 mm) diameter may be formed.

The elastomeric sleeve 44 preferably is formed from a thermoplastic rubber polymer compound of ethylene butylene styrene available from the Shell Chemical Company under the trade designation Kraton, having a durometer of Shore A 63. The sleeve 44 preferably is of the order of 0.005" (0.13 mm) wall thickness and has an inner diameter such that it will form an interference fit about the tubular segment 19. The degree of interference fit should be selected with reference to the durometer of the elastomeric sleeve 44 and the stiffness of the tubular segment 19 and should be such that the sleeve imparts a constriction about the segment to insure that the sleeve 44 will be retained in place, covering the flow passage 42. For example, an elastomeric sleeve 44 formed from Kraton may have a relaxed inner diameter of 0.018" (0.46 mm) and a wall thickness of about 0.005" (0.13 mm). The sleeve 44 is expanded and is then placed on the tubular segment 19 while in an expanded configuration. The expansion may be effected by immersing the sleeve in 1,1,2 trichlorotrifluoroethane (Freon) which will cause it to expand sufficiently that it may be placed on the tubular segment 19. As the Freon evaporates and the sleeve warms to ambient temperature, it will tend to return to its original diameter and will thereby be securely constricted about the tubular segment 19, covering the flow passage 42. The sleeve 44 should maintain a seal about the flow passage when the balloon is aspirated to about one atmosphere, as will be described. For a flow passage 42 in the form of a 1 mm longitudinally extending slit, the sleeve 44 may be several millimeters long, a 9 mm length having been found to be satisfactory. The distal end of the sleeve 44 may overlap the proximal end of the tip tube.

Alternately, the sleeve 44 may be formed from a medical grade silicone rubber tubing. Shore A 70 durometer, having an inner diameter of about 0.018" (0.46 mm), a wall thickness of about 0.009" (0.23 mm) and being about 9 mm in length. Such a sleeve similarly is expanded and placed on the tubular segment 19 in its expanded configuration and then permitted to contract about the tubular segment.

Figure 5:
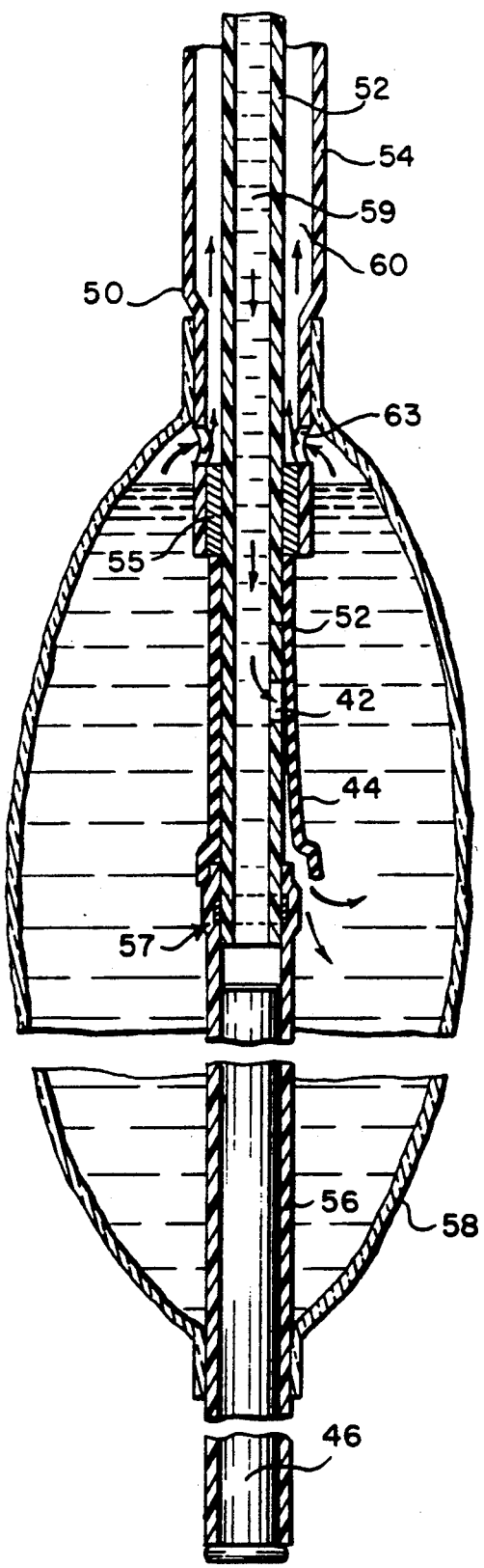
FIG. 5 is an illustration of another type of balloon catheter having a coaxial construction and embodying the invention when being purged of air.

FIG. 5 illustrates another catheter construction embodying the invention. In this construction, the catheter is coaxial in which the shaft 50 is formed from an elongate inner tube 52 and an outer tube 54 both of which may be formed from high density polyethylene. A tip tube 56 which may be formed from low density polyethylene is attached to and may be heat fused to the distal end of the inner tube 52 and protrudes distally beyond the distal end of the outer tube 54. An annular support ring 55 may be formed from a heat bondable plastic such as high density polyethylene and is disposed between the end of the outer tube 54 and the inner tube 52. The ring is heat bonded to the inner and outer tubes 52, 54. The ring 55 maintains the concentricity of the tubes. A highly radiopaque marker band 57 preferably is interposed between the overlapping portions of the tip tube and inner tube. The distal end of the tip tube terminates in a distal outlet 61. A balloon 58 is mounted to the distal end of the catheter, its proximal end being adhesively attached to the distal end of the outer tube 54 and the distal end of the balloon being adhesively attached to the distal end of the tip tube 56 by an appropriate adhesive such as cyanoacrylate. The annular space between the inner and outer tubes 52, 54 defines an inflation lumen 60 by which the balloon is inflated and deflated. A plurality of circumferentially spaced apertures 63 are formed in the outer tube 54 proximally of the ring 55 to communicate the inflation lumen 60 with the interior of the balloon. A transition member, similar to the transition member 22 of FIG. 1, is mounted to the proximal end of the catheter shaft and provides a means for communicating with the guidewire lumen 59 and the inflation lumen 60. As in the previously described embodiment an opening 42, such as a slit, is formed in the inner tube within the balloon and an elastomeric sleeve 44 is mounted on the tube over the opening as described above. The distal end of the sleeve may overlap the proximal end of the tip tube.

The catheters of both FIGS. 1 and 5 are used in conjunction with a plug 46 which may be in the form of an elongate stylet having a head 48 at one end. The manner of use of both is identical and is described with reference to FIGS. 2 and 5. The plug may be formed from stainless steel and is adapted to be inserted into the distal end of the guidewire lumen 12 to block that lumen. The plug is of a length shorter than the distance between the distal tip outlet 14 and the elastomeric sleeve 44. The plug 46 is used to temporarily obstruct the distal end of the guidewire lumen 12 while the catheter is being purged.

When setting up the catheter in preparation for an angioplasty procedure, the distal plug 46 is inserted into the guidewire lumen through the distal outlet orifice 14. While maintaining the inflation lumen 16 vented to the atmosphere through tube 26, the catheter preferably is held with the distal end pointing down as indicated in FIGS. 2 and 5 so that air in the balloon may rise to the proximal end of the balloon and be in communication with the opening 18 to the inflation lumen (FIG. 2) or openings 63 to the inflation lumen 60 (FIG. 5). Then, contrast liquid is injected, as by a syringe, into the main lumen 12 via proximal tube 24. Air in the main lumen 12 will escape through the one-way valve 41 and inflation lumen 16. As inflation liquid is pumped into the system, it will flow, under a predetermined pressure, through the opening 42 and between the sleeve 44 and the outer surface of the tubular segment 19 (FIG. 2) or inner tube 52 (FIG. 5) into the interior of the balloon 20. The valve arrangement must have a cracking pressure greater than about 1 atm (102.7 KPa) in order to assure that air will not leak into the device when the balloon is deflated, by aspiration, before inserting it into the patient. As the system is filled progressively with inflation liquid, air is purged as it escapes through the inflation lumen 16. Continued injection of inflation liquid will cause the system to become fully filled with inflation liquid, all air having escaped. By orienting the balloon downwardly, it is insured that no significant amount of air will remain entrapped within the balloon. An inflation/deflation device then may be connected to the fitting 26 for the inflation lumen 16 and the distal plug 46 is removed, the catheter thus being ready to receive a guidewire for use in the dilatation procedure. The one-way valve arrangement 41 is such that it will prevent reverse flow of inflation liquid during the range of inflation pressures that may normally be expected to be encountered, for example, up to about 20 atm (2053.6 KPa).

Thus, I have provided an improved balloon dilatation catheter having a means for rapidly and easily purging air from the balloon and inflation lumen while filling the balloon and inflation lumen with inflation liquid in readiness for a dilatation procedure. It should be understood, however, that the foregoing description of the invention is intended merely to be illustrative thereof and that other embodiments and modifications may be apparent to those skilled in the art without departing from its spirit.

Having thus described the invention, what I desire to claim and secure by letters patent is:

1. A balloon dilatation catheter comprising:
   an elongate flexible shaft having a proximal end and a distal end and a guidewire lumen open at the distal end of the shaft;
   a balloon mounted on and about the distal end of the shaft;

the shaft having an inflation lumen extending along its length, the distal end of the inflation lumen being in fluid communication with the interior of the balloon to permit inflation and deflation of the balloon; and one-way valve means on that portion of the shaft disposed within the balloon for permitting flow of liquid from the main lumen into the balloon when the liquid in the main lumen reaches a predetermined pressure while preventing reverse flow therethrough said one-way valve means being constructed and arranged to prevent said reverse flow up to pressures of the order of 20 atm.

2. A method for purging air from the balloon of a dilatation catheter comprising:

providing a catheter including an elongate flexible shaft having a proximal end and a distal end and a guidewire lumen open at the distal end of the shaft; a balloon mounted on and about the distal end of the shaft; the shaft having an inflation lumen extending along its length, the distal end of the inflation lumen being in fluid communication with the interior of the balloon to permit inflation and deflation of the balloon; and one-way valve means on that portion of the shaft disposed within the balloon for permitting flow of liquid from the main lumen into the balloon when the liquid in the main lumen reaches a predetermined pressure while preventing reverse flow therethrough;

plugging the distal opening of the guidewire lumen;

injecting liquid under pressure into the guidewire lumen under sufficient pressure to open the one-way valve means and to cause liquid to flow therethrough and to fill the balloon with liquid while permitting air to escape in a proximal direction through the inflation lumen;

after the balloon and inflation lumen are substantially filled with said liquid, unplugging the distal opening of the main lumen.

3. A method as defined in claim 2 further comprising thereafter applying a net negative pressure to the inflation lumen, said one-way valve means maintaining the flow passage closed.

4. A balloon dilatation catheter comprising:

an elongate flexible shaft having a proximal end and a distal end and a guidewire lumen open at the distal end of the shaft;

a balloon mounted on and about the distal end of the shaft;

the shaft having an inflation lumen extending along its length, the distal end of the inflation lumen being in fluid communication with the interior of the balloon to permit inflation and deflation of the balloon; and one-way valve means on that portion of the shaft disposed within the balloon for permitting flow of liquid from the main lumen into the balloon when the liquid in the main lumen reaches a predetermined pressure greater than about 1 atm while preventing reverse flow therethrough, said one-way valve means being constructed and arranged to prevent said reverse flow up to pressures of the order of 20 atm.

5. A balloon dilatation catheter comprising:

an elongate flexible shaft having a proximal end and a distal end and a guidewire lumen open at the distal end of the shaft;

a balloon mounted on and about the distal end of the shaft;

the shaft having an inflation lumen extending along its length, the distal end of the inflation lumen being in fluid communication with the interior of the balloon to permit inflation and deflation of the balloon; and one-way valve means on that portion of the shaft disposed within the balloon for permitting flow of liquid from the main lumen into the balloon when the liquid in the main lumen reaches a predetermined pressure while preventing reverse flow therethrough, said valve means comprising a flow passage formed in the wall of the shaft between the guidewire lumen and the interior of the balloon, and an elastic sleeve on the shaft disposed over the flow passage, said valve means being constructed and arranged to prevent said reverse flow up to pressures of the order of 20 atm.

6. A balloon dilatation catheter comprising:

an elongate flexible shaft having a proximal end and a distal end and a guidewire lumen open at the distal end of the shaft;

a balloon mounted on and about the distal end of the shaft;

the shaft having an inflation lumen extending along its length, the distal end of the inflation lumen being in fluid communication with the interior of the balloon to permit inflation and deflation of the balloon; and one-way valve means on that portion of the shaft disposed within the balloon for permitting flow of liquid from the main lumen into the balloon when the liquid in the main lumen reaches a predetermined pressure while preventing reverse flow therethrough, said valve means comprising a slit formed in the wall of the catheter shaft between the guidewire lumen and the interior of the balloon, and an elastic sleeve on the shaft disposed over the slit, said valve means being constructed and arranged to prevent said reverse flow up to pressures of the order of 20 atm.

7. A balloon dilatation catheter purgeable from a source of pressurized liquid, the catheter comprising:

an elongate flexible shaft having a proximal end and a distal end;

a guidewire lumen extending through the shaft, said guidewire lumen being open through the distal shaft end so that a guidewire can be extended along the guidewire lumen to project from the distal shaft end; and an inflation lumen extending from the shaft proximal end through the shaft, the inflation lumen having an opening at the shaft proximal end;

a balloon mounted on the distal end of the shaft, the balloon having an interior in fluid communication with the inflation lumen to permit inflation and deflation of the balloon with liquid;

a one-way valve connecting the guidewire lumen to the balloon interior constructed to prevent a reverse flow from the balloon interior to the guidewire lumen up to pressures of the order of 20 atm;

means for temporarily blocking the guidewire lumen opening; and means for temporarily connecting the blocked guidewire lumen to the pressurized liquid source so that pressurized liquid enters the balloon interior through the valve and causes gas in the balloon interior to exit the balloon interior by means of the inflation lumen through the inflation lumen opening at the shaft proximal end.

8. In a vascular balloon dilatation catheter having an elongate flexible shaft having a proximal end and a distal end, the shaft having a guidewire lumen extending through the shaft and being open through the distal end so that a guidewire can be extended along the guidewire lumen to project from the distal shaft end, an inflation lumen extending from the shaft proximal end through the shaft, the inflation lumen having an opening at the shaft proximal end, and a balloon mounted on the distal end of the shaft, the balloon having an interior in fluid communication with the inflation lumen to permit inflation and deflation of the balloon with liquid, apparatus for purging the balloon of gas and filling the balloon with liquid from a pressurized liquid source before insertion into a patient's vasculature, said apparatus comprising:

a one-way valve connecting the guidewire lumen to the balloon interior wherein the one-way valve comprises a slit formed in the wall of the shaft between the guidewire lumen and the balloon interior and an elastic sleeve on the shaft disposed over the slit, the elastic sleeve having sufficient elasticity that the sleeve will withstand liquid pressures in the balloon interior when the balloon is inflated on the order of 20 atmospheres without permitting a reverse flow from the balloon interior to the guidewire lumen;

means for temporarily blocking the guidewire lumen opening; and means for temporarily connecting the blocked guidewire lumen to the pressurized liquid source so that pressurized liquid enters the balloon interior through the valve and causes gas in the balloon interior to exit the balloon interior by means of the inflation lumen through the inflation lumen opening at the shaft proximal end.

* * * * *